US010987017B2

(12) United States Patent
Bouton

(10) Patent No.: US 10,987,017 B2
(45) Date of Patent: Apr. 27, 2021

(54) DISTRIBUTED EXTRAVASATION DETECTON SYSTEM

(75) Inventor: Chad E. Bouton, Powell, OH (US)

(73) Assignee: Battelle Memorial Institute, Columbus, OH (US)

(*) Notice: Subject to any disclaimer, the term of this patent is extended or adjusted under 35 U.S.C. 154(b) by 473 days.

(21) Appl. No.: 14/241,171

(22) PCT Filed: Aug. 29, 2012

(86) PCT No.: PCT/US2012/052796
§ 371 (c)(1),
(2), (4) Date: Mar. 11, 2014

(87) PCT Pub. No.: WO2013/033162
PCT Pub. Date: Mar. 7, 2013

(65) Prior Publication Data
US 2014/0371588 A1  Dec. 18, 2014

Related U.S. Application Data

(60) Provisional application No. 61/530,436, filed on Sep. 2, 2011, provisional application No. 61/530,454, filed
(Continued)

(51) Int. Cl.
A61B 5/05 (2006.01)
A61M 5/168 (2006.01)
(Continued)

(52) U.S. Cl.
CPC .......... A61B 5/0507 (2013.01); A61B 5/0022 (2013.01); A61B 5/0537 (2013.01);
(Continued)

(58) Field of Classification Search
CPC .................................... A61B 5/00; A61B 8/08
See application file for complete search history.

(56) References Cited

U.S. PATENT DOCUMENTS 3,657,656 A   4/1972  Cooper
3,779,079 A  12/1973  Snook
(Continued)

FOREIGN PATENT DOCUMENTS

CA    2470801    2/2003
CN  100482151    4/2009
(Continued)

OTHER PUBLICATIONS

Gupta, Vani; Office Action; U.S. Appl. No. 14/241,179; dated Dec. 9, p015; United States Patent and Trademark Office; Alexandria, Virginia.
(Continued)

Primary Examiner — Serkan Akar
(74) Attorney, Agent, or Firm — Stevens & Showalter LLP

(57) ABSTRACT

A system and method enhance clinical effectiveness for monitoring for a change in a level of fluid in tissue by using a device attached to a body portion that wirelessly reports to a remote apparatus or receiver a current received power level for indications of extravasation or infiltration. Adjusting an activation rate of fluid detection, reporting or both extends service life of the device.

18 Claims, 4 Drawing Sheets

Related U.S. Application Data on Sep. 2, 2011, provisional application No. 61/530,441, filed on Sep. 2, 2011.

(51) Int. Cl.

| | | |
|---|---|---|
| *A61B 5/053* | (2006.01) | |
| *A61B 5/00* | (2006.01) | |
| *A61B 8/08* | (2006.01) | |
| *A61B 5/0507* | (2021.01) | |
| *A61B 5/0537* | (2021.01) | |

(52) U.S. Cl.
CPC .......... *A61B 5/4839* (2013.01); *A61B 5/4875* (2013.01); *A61B 5/7203* (2013.01); *A61B 5/7246* (2013.01); *A61B 5/7282* (2013.01); *A61B 8/08* (2013.01); *A61M 5/16831* (2013.01); *A61M 5/16836* (2013.01); *A61B 5/4878* (2013.01); *A61B 5/6824* (2013.01); *A61M 2205/3317* (2013.01); *F04C 2270/041* (2013.01)

(56) References Cited

U.S. PATENT DOCUMENTS

| | | | |
|---|---|---|---|
| 3,951,136 A | 4/1976 | Wall | |
| 4,010,749 A | 3/1977 | Shaw | |
| 4,240,445 A | 12/1980 | Iskander et al. | |
| 4,329,689 A | 5/1982 | Yee | |
| 4,378,808 A | 4/1983 | Lichtenstein | |
| 4,488,559 A | 12/1984 | Iskander | |
| 4,572,182 A | 2/1986 | Royse | |
| 4,575,705 A | 3/1986 | Gotcher | |
| 4,637,929 A | 1/1987 | Quay | |
| 4,641,659 A | 2/1987 | Sepponen | |
| 4,647,281 A | 3/1987 | Carr | |
| 4,648,869 A | 3/1987 | Bobo, Jr. | |
| 4,653,501 A | 3/1987 | Cartmell et al. | |
| 4,667,679 A | 5/1987 | Sahota | |
| 4,690,149 A | 9/1987 | Ko | |
| 4,816,019 A | 3/1989 | Kamen | |
| 4,819,648 A | 4/1989 | Ko | |
| 4,877,034 A | 10/1989 | Atkins et al. | |
| 4,923,442 A | 5/1990 | Segall et al. | |
| 4,959,050 A | 9/1990 | Bobo, Jr. | |
| 4,971,068 A | 11/1990 | Sahi | |
| 4,993,409 A | 2/1991 | Grim | |
| 4,997,055 A | 3/1991 | Grady | |
| 5,001,436 A | 3/1991 | Scot et al. | |
| 5,026,348 A | 6/1991 | Venegas | |
| 5,184,620 A | 2/1993 | Cudahy et al. | |
| 5,191,795 A | 3/1993 | Fellingham et al. | |
| 5,255,683 A | 10/1993 | Monaghan | |
| 5,334,141 A | 8/1994 | Carr et al. | |
| 5,479,927 A | 1/1996 | Shmulewitz | |
| 5,628,322 A | 5/1997 | Mine | |
| 5,685,305 A | 11/1997 | Moonen et al. | |
| 5,769,784 A | 6/1998 | Barnett et al. | |
| 5,840,026 A | 11/1998 | Uber, III et al. | |
| 5,861,019 A | 1/1999 | Sun et al. | |
| 5,947,910 A | 9/1999 | Zimmet | |
| 5,954,668 A * | 9/1999 | Uber, III | A61M 5/16836 128/DIG. 13 |
| 5,957,950 A | 9/1999 | Mockros et al. | |
| 5,964,703 A | 10/1999 | Goodman et al. | |
| 5,995,863 A | 11/1999 | Farace et al. | |
| 6,026,173 A | 2/2000 | Svenson et al. | |
| 6,031,892 A | 2/2000 | Karellas | |
| 6,047,215 A | 4/2000 | McClure et al. | |
| 6,061,589 A | 5/2000 | Bridges et al. | |
| 6,233,479 B1 | 5/2001 | Haddad et al. | |
| 6,251,073 B1 * | 6/2001 | Imran | A61B 8/08 600/443 |
| 6,263,226 B1 | 7/2001 | Axelgaard et al. | |
| 6,300,906 B1 | 10/2001 | Rawnick et al. | |
| 6,315,719 B1 | 11/2001 | Rode et al. | |
| 6,332,087 B1 | 12/2001 | Svenson et al. | |
| 6,367,023 B2 | 4/2002 | Kling et al. | |
| 6,375,624 B1 | 4/2002 | Uber, III et al. | |
| 6,385,483 B1 | 5/2002 | Uber, III et al. | |
| 6,397,098 B1 | 5/2002 | Uber, III et al. | |
| 6,408,204 B1 | 6/2002 | Hirschman | |
| 6,415,170 B1 | 7/2002 | Loutis et al. | |
| 6,425,878 B1 | 7/2002 | Shekalim | |
| 6,454,711 B1 | 9/2002 | Haddad et al. | |
| 6,459,931 B1 | 10/2002 | Hirschman | |
| 6,487,428 B1 | 11/2002 | Culver et al. | |
| 6,520,930 B2 | 2/2003 | Critchlow et al. | |
| 6,587,428 B2 | 7/2003 | Kuribayashi | |
| 6,673,033 B1 | 1/2004 | Sciulli et al. | |
| 6,704,592 B1 | 3/2004 | Reynolds et al. | |
| 6,751,500 B2 | 6/2004 | Hirschman | |
| 6,970,735 B2 | 11/2005 | Uber, III et al. | |
| 7,047,058 B1 | 5/2006 | Dvorsky et al. | |
| 7,077,832 B2 | 7/2006 | Fleischmann | |
| 7,122,012 B2 | 10/2006 | Bouton et al. | |
| 7,221,159 B2 | 5/2007 | Griffiths et al. | |
| 7,226,415 B2 | 6/2007 | Haddad et al. | |
| 7,283,860 B2 | 10/2007 | Frazier et al. | |
| 7,431,728 B2 | 10/2008 | Gerry et al. | |
| 7,457,804 B2 | 11/2008 | Uber, III et al. | |
| 7,532,953 B2 | 5/2009 | Vogel | |
| 7,591,792 B2 | 9/2009 | Bouton | |
| 7,627,710 B1 | 12/2009 | Todd et al. | |
| 7,632,245 B1 | 12/2009 | Cowan et al. | |
| 7,674,244 B2 | 3/2010 | Kalafut et al. | |
| 7,713,239 B2 | 5/2010 | Uber, III et al. | |
| 7,937,134 B2 | 5/2011 | Uber et al. | |
| 7,996,381 B2 | 8/2011 | Uber, III et al. | |
| 8,055,328 B2 | 11/2011 | Uber, III et al. | |
| 8,160,679 B2 | 4/2012 | Uber et al. | |
| 8,182,444 B2 | 5/2012 | Uber, III et al. | |
| 8,192,397 B2 | 6/2012 | Griffiths et al. | |
| 8,295,920 B2 | 10/2012 | Bouton et al. | |
| 8,307,693 B2 | 11/2012 | Uram et al. | |
| 8,323,240 B2 | 12/2012 | Wulfman et al. | |
| 8,352,015 B2 | 1/2013 | Bernstein et al. | |
| 8,388,582 B2 | 3/2013 | Eubanks et al. | |
| 8,454,561 B2 | 6/2013 | Uber, III et al. | |
| 8,521,716 B2 | 8/2013 | Uber, III et al. | |
| 8,630,718 B2 | 1/2014 | Stahmann et al. | |
| 9,289,550 B1 | 3/2016 | Dvorsky et al. | |
| 2001/0011153 A1 * | 8/2001 | Bardy | A61B 5/0002 600/300 |
| 2001/0044588 A1 | 11/2001 | Mault | |
| 2002/0040193 A1 | 4/2002 | Hirschman | |
| 2002/0123674 A1 | 9/2002 | Plicchi et al. | |
| 2002/0172323 A1 | 11/2002 | Karellas et al. | |
| 2003/0004433 A1 | 1/2003 | Hirschman | |
| 2003/0036674 A1 * | 2/2003 | Bouton | A61B 5/05 600/12 |
| 2003/0036713 A1 | 2/2003 | Bouton et al. | |
| 2003/0120170 A1 * | 6/2003 | Zhu | A61B 5/0537 600/547 |
| 2004/0086734 A1 | 5/2004 | Janssens et al. | |
| 2004/0162488 A1 | 8/2004 | Uber, III et al. | |
| 2004/0225255 A1 * | 11/2004 | Ono | A61B 5/0059 604/65 |
| 2005/0015009 A1 | 1/2005 | Mourad et al. | |
| 2005/0073424 A1 | 4/2005 | Ruoss et al. | |
| 2005/0234428 A1 | 10/2005 | Spohn et al. | |
| 2006/0025897 A1 * | 2/2006 | Shostak | B60C 23/005 701/1 |
| 2006/0033626 A1 * | 2/2006 | Collins | G08B 25/08 340/573.1 |
| 2006/0135884 A1 | 6/2006 | Hack et al. | |
| 2006/0211970 A1 * | 9/2006 | Sciulli | A61F 13/0269 602/41 |
| 2006/0213234 A1 | 9/2006 | Gladfelter et al. | |
| 2006/0213249 A1 | 9/2006 | Uram et al. | |
| 2007/0010702 A1 | 1/2007 | Wang et al. | |
| 2007/0056871 A1 | 3/2007 | Griffiths et al. | |

(56) References Cited

U.S. PATENT DOCUMENTS

| | | | |
|---|---|---|---|
| 2007/0123770 A1* | 5/2007 | Bouton | A61B 5/0004 600/407 |
| 2007/0225601 A1 | 9/2007 | Uber, III et al. | |
| 2007/0225637 A1* | 9/2007 | Ono | A61B 5/4875 604/65 |
| 2007/0244428 A1 | 10/2007 | Uram et al. | |
| 2007/0276327 A1 | 11/2007 | Kalafut et al. | |
| 2007/0282198 A1 | 12/2007 | Uber, III et al. | |
| 2007/0282199 A1 | 12/2007 | Uber, III et al. | |
| 2008/0058680 A1 | 3/2008 | Lee et al. | |
| 2008/0058758 A1 | 3/2008 | Ranchod et al. | |
| 2008/0097339 A1 | 4/2008 | Ranchod et al. | |
| 2008/0166292 A1 | 7/2008 | Levin et al. | |
| 2008/0167900 A1 | 7/2008 | Ranchod | |
| 2008/0195060 A1 | 8/2008 | Roger et al. | |
| 2008/0294096 A1 | 11/2008 | Uber, III et al. | |
| 2009/0015353 A1 | 1/2009 | Rofougaran | |
| 2009/0070342 A1 | 3/2009 | Uber, III et al. | |
| 2009/0177050 A1 | 7/2009 | Griffiths et al. | |
| 2009/0247866 A1 | 10/2009 | Uber, III et al. | |
| 2009/0276327 A1 | 11/2009 | Malik | |
| 2009/0299175 A1 | 12/2009 | Bernstein et al. | |
| 2009/0326370 A1 | 12/2009 | Uber, III et al. | |
| 2010/0049004 A1* | 2/2010 | Edman | A61B 5/1118 600/300 |
| 2010/0113887 A1 | 5/2010 | Kalafut et al. | |
| 2010/0114064 A1 | 5/2010 | Kalafut et al. | |
| 2010/0160786 A1 | 6/2010 | Nordgren et al. | |
| 2010/0174179 A1* | 7/2010 | Persson | A61B 5/05 600/430 |
| 2010/0185040 A1 | 7/2010 | Uber, III et al. | |
| 2010/0198141 A1 | 8/2010 | Laitenberger et al. | |
| 2010/0256462 A1* | 10/2010 | Rappaport | A61B 5/00 600/301 |
| 2011/0002802 A1 | 1/2011 | Capone et al. | |
| 2011/0130800 A1 | 6/2011 | Weinstein et al. | |
| 2011/0257522 A1 | 10/2011 | Berard-Andersen et al. | |
| 2012/0019386 A1 | 1/2012 | Doraiswami et al. | |
| 2013/0062528 A1 | 3/2013 | Hyde et al. | |
| 2013/0079581 A1 | 3/2013 | Agamaite et al. | |
| 2013/0123567 A1 | 5/2013 | Agamaite et al. | |
| 2013/0123614 A1 | 5/2013 | Bernstein et al. | |
| 2013/0131585 A1 | 5/2013 | Eubanks et al. | |
| 2013/0190646 A1 | 7/2013 | Weinstein et al. | |
| 2013/0231550 A1 | 9/2013 | Weinstein et al. | |
| 2013/0253254 A1 | 9/2013 | Uber, III et al. | |
| 2013/0255390 A1 | 10/2013 | Riley et al. | |
| 2013/0274599 A1 | 10/2013 | Bouton et al. | |
| 2013/0331634 A1 | 12/2013 | Kaintz et al. | |
| 2013/0331635 A1 | 12/2013 | Hoffman et al. | |
| 2013/0331810 A1 | 12/2013 | Bazala et al. | |
| 2013/0345676 A1 | 12/2013 | Wulfman et al. | |
| 2014/0046295 A1 | 2/2014 | Uber, III et al. | |
| 2014/0228686 A1 | 8/2014 | Bouton | |
| 2020/0315492 A1 | 10/2020 | Bouton | |

FOREIGN PATENT DOCUMENTS

| | | |
|---|---|---|
| DE | 4007587 | 9/1991 |
| EP | 1472973 | 11/2004 |
| EP | 1647306 | 4/2006 |
| EP | 2455402 | 5/2012 |
| EP | 2526857 | 11/2012 |
| EP | 2750594 | 7/2014 |
| EP | 2750595 | 7/2014 |
| GB | 2251080 | 6/1992 |
| JP | 1157001 | 3/1999 |
| JP | 2007509353 | 4/2007 |
| WO | 9926685 | 6/1999 |
| WO | 9926686 | 6/1999 |
| WO | 9929356 | 6/1999 |
| WO | 0108729 | 2/2001 |
| WO | 2003000972 A1 | 1/2003 |
| WO | 03009752 | 2/2003 |
| WO | 03063680 | 8/2003 |
| WO | 2004036467 | 4/2004 |
| WO | 2005043100 | 5/2005 |
| WO | 03009753 | 2/2006 |
| WO | 2008100670 | 8/2008 |
| WO | 2009009753 A1 | 1/2009 |
| WO | 20100146372 | 12/2010 |
| WO | 2011067623 | 6/2011 |
| WO | 2011067685 | 6/2011 |
| WO | 2012011065 | 1/2012 |
| WO | 2012011066 | 1/2012 |
| WO | 2012059929 | 5/2012 |
| WO | 2013033162 | 3/2013 |
| WO | 2013033166 | 3/2013 |
| WO | 2013033174 | 3/2013 |
| WO | 2013093923 | 6/2013 |
| WO | 2013147799 | 10/2013 |

OTHER PUBLICATIONS

Gupta, Vani; First Office Action, U.S. Appl. No. 14/241,203; dated Oct. 5, 2015; United States Patent and Trademark Office; Alexandria, VA.

Carr, Kenneth L.; Use of Gallium Arsenide in Medical Applications: Microwave Medical Systems, Inc.; GaAs IC Symposium; pp. 10-13; 1999 IEEE.

Shaeffer, James et al.; Early Detection of Extravasation of Radiographic Contrast Medium; Radiology; pp. 141-144; Jul. 1992.

Chad E. Bouton; U.S. Appl. No. 14/241,179, filed Mar. 11, 2014 entitled Wireless and Power-Source-Free Extravasation and Infiltration Detection Sensor; United States Patent and Trademark Office; Alexandria, VA (National Stage of PCT/US2012/052801 filed Aug. 29, 2012).

De la Hera, German; International Search Report and Written Opinion; International Application No. PCT/US2012/052796; dated Dec. 10, 2012; European Patent Office.

De la Hera, German; International Search Report and Written Opinion; International Application No. PCT/US2012/052801; dated Dec. 19, 2012; European Patent Office.

De la Hera, German; International Search Report and Written Opinion; International Application No. PCT/US2012/052813; dated Dec. 7, 2012; European Patent Office.

Shaeffer, James et al.; Detection of Extravasation of Antineoplastic Drugs by Microwave Radiometry; Cancer Letter, 31; pp. 284-291; 1986; Elsevier Scientific Publishers Ireland Ltd.

Sukamto, Lin M. et al.; MMIC Receiver for Water-Vapor Radiometer; NASA Tech Briefs; p. 34; Sep. 1993.

Arkin, H. et al.; Recent Developments in Modeling Heat Transfer in Blood Perfused Tissues; IEEE Transactions on Biomedical Engineering; vol. 41, No. 2; pp. 97-107; Feb. 1994.

Harris, Thomas S. et al.; Infusion Line Model for the Detection of Infiltration Extravasation, and other Fluid Flow Faults; IEEE Transactions on Biomedical Engineering; vol. 40, No. 2; pp. 154-162; Feb. 1993.

Montreuil, Jean et al.; Multiangle Method for Temperature Measurement of Biological Tissues by Microwave Radiometry; IEEE Transactions on Microwave Theory and Techniques; vol. 39, No. 7; pp. 1235-1238; Jul. 1991.

Lin, James C. et al.; Microwave Imaging of Cerebral Edema; Proceedings of the IEEE; vol. 70, No. 5; pp. 523-524; May 1982.

Kramer, Gerhard G. et al.; Dielectric Measurement of Cerebral Water Content Using a Network Analyzer; Neurological Research; vol. 14, No. 3; pp. 255-258; Sep. 1992.

Ling, Geoffrey S.F. et al.; Diagnosis of Subdural and Intraparenchymal Intracranial Hemorrhage Using a Microwave Based Detector; Digitization of the Battlespace V and Battlefield Biomedical Technologies II; vol. 4037; pp. 212-217; Apr. 24, 2000.

Behari, J. et al.; Dielectric Permittivity of Biological Tissues in the Microwave Frequency Range; Proceedings of the SPIE—The International Society for Optical Engineering, Advanced Microwave and Millimeter-Wave Detectors; vol. 2275; pp. 301-308; San Diego, CA; Jul. 25-26, 1994.

(56) References Cited

OTHER PUBLICATIONS

Andreuccetti, D. et al.; High Permittivity Patch Radiator for Single and Multi-Element Hyperthermia Applicators; IEEE Transactions on Biomedical Engineering; vol. 40, No. 7; pp. 711-715; IEEE Inc.; New York; Jul. 1, 1993'.
Lee, Eric R. et al.; Body Conformable 915 MHz Microstrip Array Applicators for Large Surface Area Hyperthermia; IEEE Transactions on Biomedical Engineering; vol. 39, No. 5; pp. 470-438; IEEE Inc., New York; May 1, 1992.
Jameson, P.; International Search Report; Application No. PCT/US00/20112; dated Oct. 17, 2000; European Patent Office.
Van Dooren, G.; International Search Report; Application No. PCT/US02/23877; dated Feb. 6, 2003; European Patent Office.
Beitner, M.; International Search Report; Application No. PCT/US02/23925; dated Jan. 15, 2003; European Patent Office.
P.B. James and R.W. Galloway; The Ultrasonic Blood Velocity Detector as an Aid to Arteriography; Br J Radiol; Oct. 1971; 44:743-746.
European Search Report for EP12005361 dated Mar. 6, 2013.
Bouton, Chad E.: Final Office Action; U.S. Appl. No. 13/620,310; dated Jan. 6, 2014; United States Patent and Trademark Office; Alexandria, VA.
Supplementary European Search Report for EP04796177 dated May 11, 2010.
Partial European Search Report for EP12005361 dated Nov. 2, 2012.
Kent: "Hand-Held Instrument for Fat/Water Determination in Whole Fish"; 1993; at http://distell.com/products/prd-fish-fatmeter/technical-data/ffm-research-paper.
Birnbaum et al.: "Extravasation Detection Accessory: Clinical Evaluation in 500 Patients"; 1999; Radiology 212:431-438.
"Value of Multi-Detector Array CT in the Assessment of Portal Hypertension"; Portal Hypertension: Diagnostic Imaging and Imaging-Guided Therapy (Medical Radiology/Diagnostic Imaging).; Ed. Plinio Rossi. 1st ed.; Springer; 2000; p. 111.
International Preliminary Report on Patentability and Written Opinion dated Oct. 5, 2005 for PCT/US2004/35135.
International Search Report for PCT/US2004/035135 dated Oct. 5, 2005.
Gupta, Vani; Final Office Action, U.S. Appl. No. 14/241,203; dated May 6, 016; United States Patent and Trademark Office; Alexandria, VA.
Gupta, Vani; Office Action; U.S. Appl. No. 14/241,203; dated Aug. 30, 016; United States Patent and Trademark Office; Alexandria, Virginia.
Gupta, Vani; Final Office Action; U.S. Appl. No. 14/241,203; dated Apr. 21, 2017; United States Patent and Trademark Office, Alexandria, Virginia.
Gupta, Vani; Office Action; U.S. Appl. No. 14/241,179; dated May 22, 2017; United States Patent and Trademark Office, Alexandria, Virginia.
Gupta, Vani; Non-final Office Action; U.S. Appl. No. 14/241,203; dated Mar. 13, 2018; United States Patent and Trademark Office, Alexandria, Virginia.
IP, Jason M.; Final Office Action; U.S. Appl. No. 13/620,310; dated Mar. 5, 2018; United States Patent and Trademark Office; Alexandria, VA.
IP, Jason M.; Office Action; U.S. Appl. No. 13/620,310; dated Jul. 27, 2017; United States Patent and Trademark Office; Alexandria, VA.
IP, Jason M.; Final Office Action; U.S. Appl. No. 13/620,310; dated Jun. 14, 2016; United States Patent and Trademark Office; Alexandria, VA.
IP, Jason M.; Advisory Action; U.S. Appl. No. 13/620,310; dated May 5, 2016; United States Patent and Trademark Office; Alexandria, VA.
IP, Jason M.; Final Office Action; U.S. Appl. No. 13/620,310; dated Feb. 5, 2016; United States Patent and Trademark Office; Alexandria, VA.
IP, Jason M.; Office Action; U.S. Appl. No. 13/620,310; dated May 29, 2015; United States Patent and Trademark Office; Alexandria, VA.
IP, Jason M.; Final Office Action; U.S. Appl. No. 13/620,310; dated Aug. 7, 2014; United States Patent and Trademark Office; Alexandria, VA.
IP, Jason M.; Office Action; U.S. Appl. No. 13/620,310; dated Apr. 23, 2014; United States Patent and Trademark Office; Alexandria, VA.
IP, Jason M.; Office Action; U.S. Appl. No. 13/620,310; dated Sep. 9, 2013; United States Patent and Trademark Office; Alexandria, VA.
Bor, Helene Catherine; Notice of Allowance; U.S. Appl. No. 11/385,448; dated Nov. 20, 2015; United States Patent and Trademark Office; Alexandria, VA.
Bor, Helene Catherine; Final Office Action; U.S. Appl. No. 11/385,448; dated Jun. 3, 2015; United States Patent and Trademark Office; Alexandria, VA.
Bor, Helene Catherine; Office Action; U.S. Appl. No. 11/385,448; Sep. 30, 2014; United States Patent and Trademark Office; Alexandria, VA.
Bor, Helene Catherine; Office Action; U.S. Appl. No. 11/385,448; dated Jan. 6, 2014; United States Patent and Trademark Office; Alexandria, VA.
Bor, Helene Catherine; Final Office Action; U.S. Appl. No. 11/385,448; Jul. 18, 2013; United States Patent and Trademark Office; Alexandria, VA.
Bor, Helene Catherine; Office Action; U.S. Appl. No. 11/385,448; dated Dec. 28, 2012; United States Patent and Trademark Office; Alexandria, VA.
Bor, Helene Catherine; Advisory Action; U.S. Appl. No. 11/385,448; dated Aug. 29, 2011; United States Patent and Trademark Office; Alexandria, VA.
Fontenot, Nigel Rai; Final Office Action; U.S. Appl. No. 11/385,448; dated Mar. 28, 2011; United States Patent and Trademark Office; Alexandria, VA.
Fontenot, Nigel Rai; Office Action; U.S. Appl. No. 11/385,448; dated Dec. 3, 2010; United States Patent and Trademark Office; Alexandria, VA.
Fontenot, Nigel Rai; Final Office Action; U.S. Appl. No. 11/385,448; dated Feb. 24, 2010; United States Patent and Trademark Office; Alexandria, VA.
Fontenot, Nigel Rai; Final Office Action; U.S. Appl. No. 11/385,448; dated Sep. 30, 2009; United States Patent and Trademark Office; Alexandria, VA.
Fontenot, Nigel Rai; Final Office Action; U.S. Appl. No. 11/385,448; dated May 13, 2009; United States Patent and Trademark Office; Alexandria, VA.
Fontenot, Nigel Rai; Final Office Action; U.S. Appl. No. 11/385,448; dated Nov. 13, 2008; United States Patent and Trademark Office; Alexandria, VA.
Gupta, Vani; Final Office Action; U.S. Appl. No. 14/241,179; dated May 18, 2018; United States Patent and Trademark Office; Alexandria, VA.
Gupta, Vani; Office Action; U.S. Appl. No. 14/241,179; dated Nov. 28, 2018; United States Patent and Trademark Office; Alexandria, VA.
Gupta, Vani; Office Action; U.S. Appl. No. 14/241,203; dated Nov. 20, 2018; United States Patent and Trademark Office; Alexandria, VA.
De la Hera, German; Official Action; European Patent Application No. 12759562.7; dated Oct. 5, 2018; European Patent Office, Munich, Germany.
De la Hera, Germán; Examination Report; European Patent Application No. 12772147.0; dated Oct. 8, 2018; European Patent Office, Munich, Germany.
Akar, Serkan; Office Action; U.S. Appl. No. 14/241,203; dated Aug. 23, 2019; U.S. Patent and Trademark Office; Alexandria, Virginia.
Akar, Serkan; Notice of Allowance; U.S. Appl. No. 14/241,179; dated Aug. 13, 2019; U.S. Patent and Trademark Office; Alexandria, Virginia.
EPO Examination Report; European Patent Application No. 12759562.7; dated Feb. 4, 2020; European Patent Office; Munich, Germany.

(56) References Cited

OTHER PUBLICATIONS

Chad E. Bouton; Related U.S. Appl. No. 17/072,428, filed Oct. 16, 2020 entitled Extravasation and Infiltration Detection Device.
Gupta, Vani; Office Action; U.S. Appl. No. 14/241,179; dated Oct. 11, 2016; United States Patent and Trademark Office, Alexandria, Virginia.
Chad E. Bouton; Related U.S. Appl. No. 17/249,321, filed Feb. 26, 2021 entitled "Distributed Extravasation Detection System".

* cited by examiner

DISTRIBUTED EXTRAVASATION DETECTON SYSTEM

TECHNICAL FIELD

The present invention relates generally to the detection of fluids in tissue, and, more particularly, to apparatuses, systems and methods for detection of changed, elevated or abnormal fluid levels in tissue.

BACKGROUND ART

Changed, elevated or abnormal fluid levels in living tissue can result from a number of physiological conditions. For example, edema is an abnormal accumulation of watery fluid in the intercellular spaces of connective tissue. Edematous tissues are swollen and, when punctured, secrete a thin incoagulable fluid. Edema is most frequently a symptom of disease rather than a disease in itself, and it may have a number of causes, most of which can be traced back to gross variations in the physiological mechanisms that normally maintain a constant water balance in the cells, tissues, and blood. Among the causes may be diseases of the kidneys, heart, veins, or lymphatic system; malnutrition; or allergic reactions.

Moreover, bleeding (hemorrhage) can cause blood to collect and clot (hematoma). Hematomas can, for example, occur beneath the outermost of three membranes that cover the brain (meninges) as a result of a head injury. There are two types of cranial subdural hematomas. An acute subdural hematoma occurs soon after a severe head injury. A chronic subdural hematoma is a complication that may develop weeks after a head injury. Such a head injury may have been so minor that the patient does not remember it. An epidural hematoma is a traumatic accumulation of blood between the inner table of the skull and the stripped-off dural membrane. The inciting event often is a focused blow to the head. It is often difficult to detect hematomas, particularly when the hematoma occurs well after the time of an injury.

In addition to accumulation of body fluids, elevated fluid levels in tissue can arise as a result of introduction of a fluid into the body, for example, during an injection procedure. In that regard, in many medical diagnostic and therapeutic procedures, a physician or other person injects fluid into a patient's blood vessels. Moreover, in recent years, a number of injector-actuated syringes and powered injectors for pressurized injection of contrast medium in procedures such as angiography, computed tomography, ultrasound and NMR/MRI (Nuclear Magnetic Resonance/Magnetic Resonance Imaging) have been developed.

Extravasation or infiltration is the accidental infusion or leakage of an injection fluid such as a contrast medium or a therapeutic agent into tissue surrounding a blood vessel rather than into the blood vessel itself. Extravasation can be caused, for example, by rupture or dissection of fragile vasculature, valve disease, inappropriate needle placement, or patient movement resulting in the infusing needle being pulled from the intended vessel or causing the needle to be pushed through the wall of the vessel. High injection pressures and/or rates of some modem procedures can increase the risk of extravasation. In computed tomography, for example, contrast injection flow rates can be in the range of 0.1 to 10 ml/s.

Extravasation can cause serious injury to patients. In that regard, certain injection fluids such as contrast media or chemotherapy drugs can be toxic to tissue. It is, therefore, very important when performing fluid injections to detect extravasation as soon as possible and discontinue the injection upon detection.

In U.S. Pat. No. 7,122,012 to Bouton, et al., issued Oct. 17, 2006, which is hereby incorporated by reference in its entirety, a method was disclosed for detecting a change in the level of fluid in tissue in a first area of a body. Steps included applying electromagnetic energy, preferably in the frequency range of approximately 300 MHz to approximately 30 GHz, to a first volume of the body; measuring a resultant or returned signal; comparing the signal to a reference signal to determine if the fluid level in the tissue has changed. In one embodiment, the method detected changes in the level of fluid in tissue of a body by applying electromagnetic energy to a first volume of the body over a period of time; measuring a resultant signal or a signal returned from the tissue; and comparing the signal to a reference signal to determine if a level of fluid in the tissue has changed during the period of time.

DISCLOSURE OF INVENTION

The following presents a simplified summary in order to provide a basic understanding of some aspects of the disclosed aspects.

In accordance with one or more aspects and embodiments, and the corresponding disclosures thereof, various features of the invention are described in connection with detecting a change in the level of fluid in tissue of a body with an apparatus having a wireless link for remote monitoring. In particular, extravasation during a fluid injection or infiltration during fluid infusion into a body part is detected with the flexibility of being spaced away from a receiver that gives an indication to care givers. By using a wireless link, a patient, for example, can be mobile, especially for lower fluid rate infusions. Alternatively or in addition, multiple patients can be collectively monitored, recorded, analyzed, etc., leveraging an institutional infrastructure.

Enabling this flexibility, an apparatus or integrated device is largely or entirely worn by the patient undergoing the injection or infusion. The device can be adjusted to vary a rate of detection and reporting. Thereby, power can be conserved and potentially the increased ambient noise from multiple integrated devices can be reduced without impairing timely detection of an extravasation or infiltration.

In one aspect, the present disclosure provides an apparatus for indicating a change in a level of fluid in tissue of a body. A detecting component transmits power into and receives power from a body portion, wherein a change in the received power that passes through the tissue is indicative of a change in the fluid level. A signal processing component generates an output signal based at least in part on the received signal. A wireless interface transmits, to a receiver, the output signal from the signal processing component. The apparatus advantageously further comprise a power supply that powers the detecting component and the wireless interface.

The apparatus may further comprise a conduit for providing fluid to the body. In various aspects and embodiments, a substrate may be provided to support one or more of the detecting component, the signal processing component, the wireless interface and the conduit. In some embodiments all of these components may be supported by the substrate. In other embodiments, the conduit may be positioned near the substrate but is not supported on the substrate.

A current received power level may be defined by only the received power when the transmitted power is fixed and there are no changes, except for fluid level, in the pathway from structure forming part of the detecting component that transmits the power into the body portion and structure forming part of the detecting component that receives the power passing through the body portion. Alternatively, when the transmitted power varies during a time period of interest, the current received power level may be defined as a ratio of the received power to the transmitted power, presuming good coupling of the detecting component to the tissue. A decrease in the received power level represents an increase in fluid level.

In some embodiments, the detecting component comprises a control component for intermittently causing power to be transmitted to the body portion. For instance, the control component can comprise an adjustment feature for setting a period between intermittent activations.

In some embodiments, the wireless interface intermittently reports the output signal. For instance, the signal processing component can receive a reference signal from the detecting component and compare the reference signal with a signal corresponding to the received power for generating the output signal.

In embodiments of the invention, a comparison component may be provided to receive a control input, set a baseline received power level based on the received power in response to the control input, compare a current received power level at a subsequent time with the baseline level to produce a comparison result, and generate the output signal based upon the comparison result. In some embodiments, a substrate is provided to support the detecting component and the wireless interface. For instance, the power supply may comprise a portable power supply supported by the substrate.

In some embodiments, the detecting component further transmits power and receives power comprising a Radio Frequency (RF) signal. For instance, the detecting component comprises an RF voltage controlled oscillator for sweeping a frequency range of greater than 1.5 GHz to approximately 10 GHz over a period of time. Alternatively or in addition, the detecting component further comprises a gain/phase measurement circuit. The detecting component may comprise a transmit antenna for transmitting power comprising a Radio Frequency (RF) signal and a receive antenna for receiving power comprising an RF signal.

In some embodiments, the detecting component further transmits power and receives power comprising an ultrasonic signal.

In further embodiments, the wireless interface comprises at least one of a personal area network interface, a Wi-Fi interface, and a cellular interface. For instance, the wireless interface can comprise the personal area network interface that interfaces to a cellular device for communicating with the receiver.

In a second aspect, a system is provided for indicating a change in a level of fluid in tissue of a body. The system may comprise the apparatus of any of the embodiments described in relation to the first aspect of the invention. In an embodiment of this aspect, the system may comprise a device/apparatus comprising a detecting component for transmitting power into and receiving power from the body portion, a signal processing component for generating an output signal based at least in part on the received power, and a wireless interface for transmitting the output signal from the signal processing component. Conveniently, the device/apparatus of this and the first aspect of the invention may be attachable to a body portion, in use. The system typically further comprises a power supply for powering the detecting component, the signal processing component and the wireless interface. The system may further comprise a remote apparatus comprising a receiver for receiving the output signal from the wireless interface.

In embodiments of the invention, the remote apparatus may further comprise a comparison component for receiving a control input, setting a baseline received power level based on a current received power level in response to the control input, comparing the current received power level at a subsequent time with the baseline level to produce a comparison result, and generating an indication of fluid level change based upon the comparison result.

In other embodiments, the device further comprises a comparison component for receiving a control input, setting a baseline current power level based on a current power level in response to the control input, comparing the current level at a subsequent time with the baseline level to produce a comparison result, and generating the output signal based upon the comparison result.

In a third aspect, the present invention provides a method for detecting a change in a level of fluid in tissue of a body. Conveniently, the method employs as apparatus and/or system according to the invention. A power waveform is transmitted into a body portion. Power is received from the body portion. A baseline received power level and a subsequent series of current received power levels are determined from the transmitted and received power. The current level is compared with the baseline level. A reporting rate is determined, comprising at least a first rate for reduced power consumption and a second rate for increased reporting. An output signal is transmitted at the reporting rate that is related to the current level to a receiver.

In some suitable embodiments, the method further provides for setting the reporting rate based upon a user setting.

To the accomplishment of the foregoing and related ends, one or more aspects comprise the features hereinafter fully described and particularly pointed out in the claims. The following description and the annexed drawings set forth in detail certain illustrative aspects and are indicative of but a few of the various ways in which the principles of the aspects may be employed. Other advantages and novel features will become apparent from the following detailed description when considered in conjunction with the drawings and the disclosed aspects are intended to include all such aspects and their equivalents.

BRIEF DESCRIPTION OF DRAWINGS

The disclosed aspects will hereinafter be described in conjunction with the appended drawings, provided to illustrate and not to limit the disclosed aspects, wherein like designations denote like elements, and in which.

MODES FOR CARRYING OUT THE INVENTION

A system and method enhance clinical effectiveness for monitoring for a change in a level of fluid in tissue by using a device attached to a body portion that wirelessly reports to a remote apparatus or receiver for indications of extravasation or infiltration. Adjusting an activation rate of fluid detection, reporting or both extends service life of the device. Embodiments of the device can include Radio Frequency (RF) transmission for changes in permittivity or ultrasonic measurements. Remote monitoring and indication leverages institutional monitoring systems to ensure that a state of extravasation or infiltration is addressed in a timely fashion.

Various aspects are now described with reference to the drawings. In the following description, for purposes of explanation, numerous specific details are set forth in order to provide a thorough understanding of one or more aspects. It may be evident, however, that such aspect(s) may be practiced without these specific details.

Figure 1:
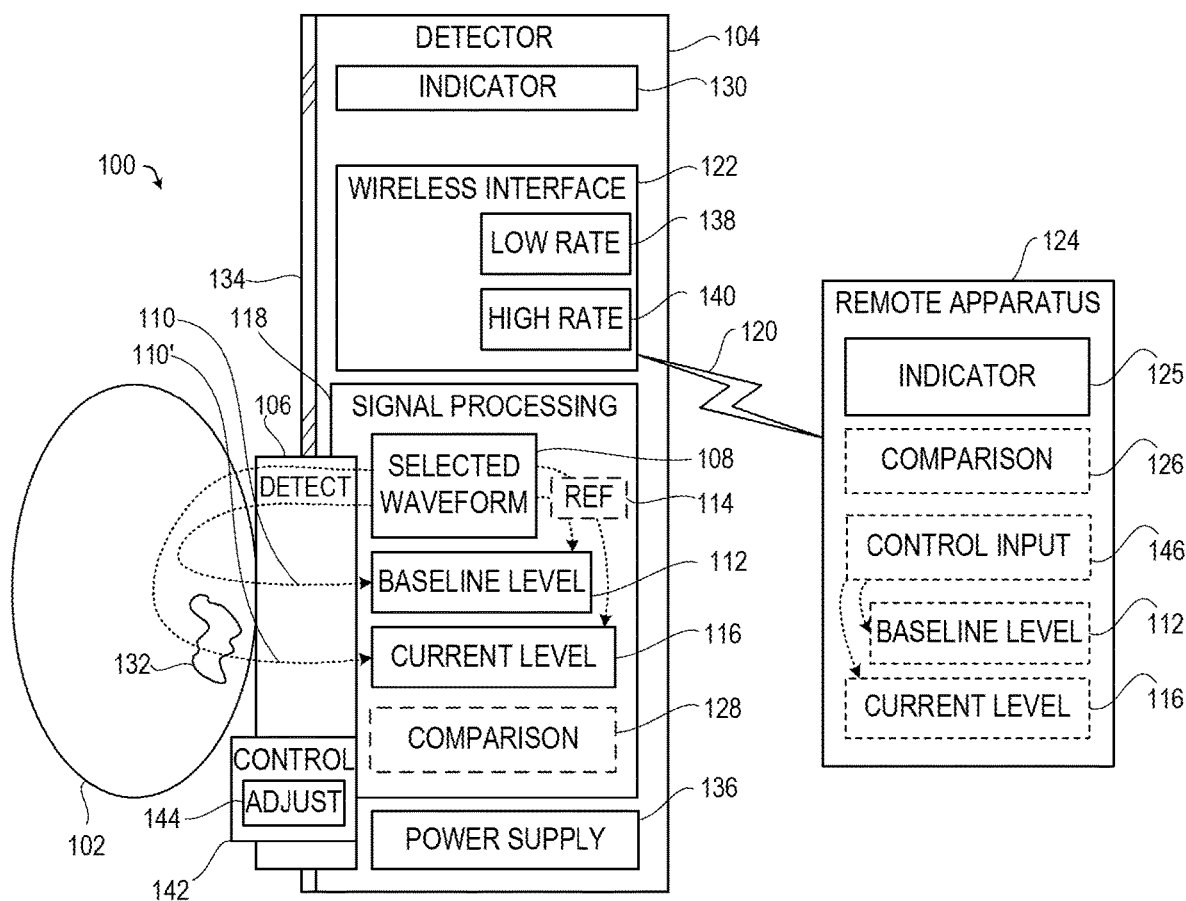
FIG. 1 is a schematic block diagram of a system for detecting a change in a fluid level in tissue, according to one aspect.

In FIG. 1, a system 100 detects a change in a level of fluid in tissue of a body portion 102. For example, at an initial time, such as before beginning a fluid injection or infusion, a device 104 having a detecting component 106 is attached to the body portion 102 for passing a selected waveform 108 (e.g., microwave, acoustic) as transmitted power that encounters a baseline level of fluid and tissue. A baseline received power level 112 corresponding to the baseline fluid level can be based upon an absolute measurement of received power 110 that has passed through body tissue or based upon a comparison of the received power 110 through body tissue with a reference signal 114 of the selected waveform 108, such as for amplitude and/or phase information. At a subsequent time or series of times, the selected waveform 108 as received power 110' through the body portion 102 is detected and a current received power level 116 corresponding to a current fluid level can be based upon an absolute measurement of the received power 110' through the body tissue or a comparison of the received power through body tissue relative to the reference signal 114.

A signal processing component 118 is coupled to the detecting component 106 for generating an output signal 120 for wireless transmission by a wireless interface 122 of the device 104. A remote apparatus or receiver 124 that receives the output signal 120 can generate an alert via an indicator 125 if the output signal 120 contains an indication of certain states of the device 104 (e.g., inoperative, nominal, etc.) or body portion 102 (e.g., normal fluid level, increased fluid level, etc.). Thus, the output signal 120 is indicative of the received power 110, 110' as detected by the detecting component 106.

In one aspect, the output signal 120 can be representative of, or related to, an absolute measurement of the received power 110, 110'. Alternatively, the output signal 120 can be representative of, or related to, a relative measurement of the received power 110, 110' as compared to the reference signal 114. The output signal 120 at a specified time can be designated the baseline received power level 112 and subsequently can provide the current received power level 116 for signal processing by a comparison component 126 in the remote apparatus or receiver 124. Tracking of the baseline level 112 and the current level 116 can be performed at the remote apparatus or receiver 124 for use by the comparison component 126. Thus, in an exemplary aspect, the comparison component 126 of the remote apparatus or receiver 124 receives a control input 146 such as when the device 104 is initially activated so as to set a baseline received power level 112 corresponding to a baseline fluid level based on the current received power level 116 in response to receiving the control input 146, compares the current received power level 116 corresponding to a current fluid level at a subsequent time with the baseline level 112 to produce a comparison result, and generates an indication of fluid level change based upon the comparison result.

Alternatively or in addition, the device 104 can incorporate additional signal processing capabilities, depicted as a local comparison component 128 of the signal processing component 118. Thus, the output signal 120 can comprise discrete values indicating a state of the device 104 (e.g., inoperative, nominal, etc.) or body portion 102 (e.g., normal, increased fluid level, etc.). These discrete values can be indicated on a local indicator 130, wirelessly transmitted as an output signal 120 for indicating on indicator 125, or both. Alternatively a range or continued set of values can be indicated or reported.

In another exemplary aspect, the local comparison component 128 of the device 104 receives a local control input, such as a manual input to define a baseline received power level corresponding to a baseline fluid level, or the control input 146 from the remote apparatus or receiver 124. In response, the device 104 sets the baseline received power level 112 based on the current received power level 116 in response to the control input 146, compares the current level 116 at a subsequent time with the baseline level 112 to produce a comparison result, and generates the output signal 120 based upon the comparison result.

In use, the received power 110' used for the current received power level 116 can be essentially unchanged from the received power 110 used for the baseline received power level 112. Qualities of the current level 116 can serve nonetheless as an affirmation that no state of extravasation or infiltration exists and that the device 104 is operating nominally.

In some instances, the received power 110' can encounter an area 132 of a changed (e.g., increased) level of fluid. The area 132 can cause swelling and changes in transmission of the received power 110', such as affecting ultrasonic and microwave transmission characteristics. Typically, an increase in fluid level in the area 132 results in a reduction in the amount of received power 110' detected by the detection component 106. If the transmitted power from the detecting component 106 is constant over the time of the period of interest, then the absolute measurement of the propagated power 110' may define the current received power level 116. If the transmitted power varies over the time of the period of interest, then the current level 116 should be based on a comparison of the propagated power 110' to the reference signal 114. Thereby, the current level 116 represents a change in the baseline received power level 112 corresponding to a baseline fluid level that can warrant an alert if the change in the current received power level 116 from the baseline level 112, indicating a fluid level change, falls below a threshold, e.g., the current level 116 is equal to or less than 90% of the baseline level 112.

In an exemplary aspect, the device 104 comprises an integrated assembly wherein a substrate 134 functions to attach the detecting component 106 to the body portion 102, e.g., an outer surface of the body portion, as well as supporting other parts or the entirety of the device 104, which can include a power supply 136 for powering the detecting component 106, the signal processing component 118 and the wireless interface 122. For example, the power supply 136 can be portable (e.g., rechargeable battery). In order to provide long-term reliability and reduced maintenance requirements, the wireless interface 122 can report at more than one rate, depicted as low rate 138 and high rate 140, although it should be appreciated that a greater range of reporting could be provided and selected. It is also contemplated that a conduit (e.g., catheter, needle, etc.) may be mounted to the substrate 134 so as to provide fluid to a body portion from a fluid supply (e.g., infuser supply, contrast agent injector, IV drip, etc.). It is further contemplated that the fluid providing conduit may not be coupled to the substrate 134 but may be positioned near the substrate 134.

Changing the frequency of activating the detecting component 106, the wireless interface 122, or both, between the high rate 140 and the low rate 138 mitigates power consumption. To that end, the detecting component 106 can comprise a control component 142 for intermittently causing power to be transmitted to the body portion 102. For instance, the control component 142 can comprise a manual adjustment feature 144 for setting a period between intermittent activations, which may relate to a rate of fluid injection or transfusion. In another exemplary aspect, the wireless interface 122 intermittently reports the output signal 120, which rate may be adjustable as well.

By virtue of the foregoing, the device 104 comprises the detecting component 106 for transmitting power into and receiving received power 110, 110' from the body portion 102 for sensing the current received power level 116, the signal processing component 118 for generating the output signal 120 based at least in part on the received or detected power 110, 110', the wireless interface 122 for transmitting the output signal 120 from the signal processing component 118, and the power supply 136 for powering the detecting component 106, the signal processing component 118 and the wireless interface 122. The remote apparatus or receiver 124 receives the output signal 120 from the wireless interface 122.

In another exemplary aspect, the detecting component 106 further transmits power and receives power comprising a Radio Frequency (RF) signal. For instance, the detecting component comprises an RF voltage controlled oscillator for sweeping a frequency range of greater than 1.5 GHz to approximately 10 GHz over a period of time. Alternatively or in addition, the detecting component 106 further comprises a gain/phase measurement circuit.

In an additional exemplary aspect, the detecting component 106 further transmits power and receives power comprising an ultrasonic signal.

In a further exemplary aspect, the wireless interface 122 comprises at least one of a personal area network (PAN) interface, a Wi-Fi interface, and a cellular interface. For instance, the wireless interface 122 can comprise the PAN interface that interfaces to a cellular device for communicating with the remote apparatus or receiver 124.

Figure 2:
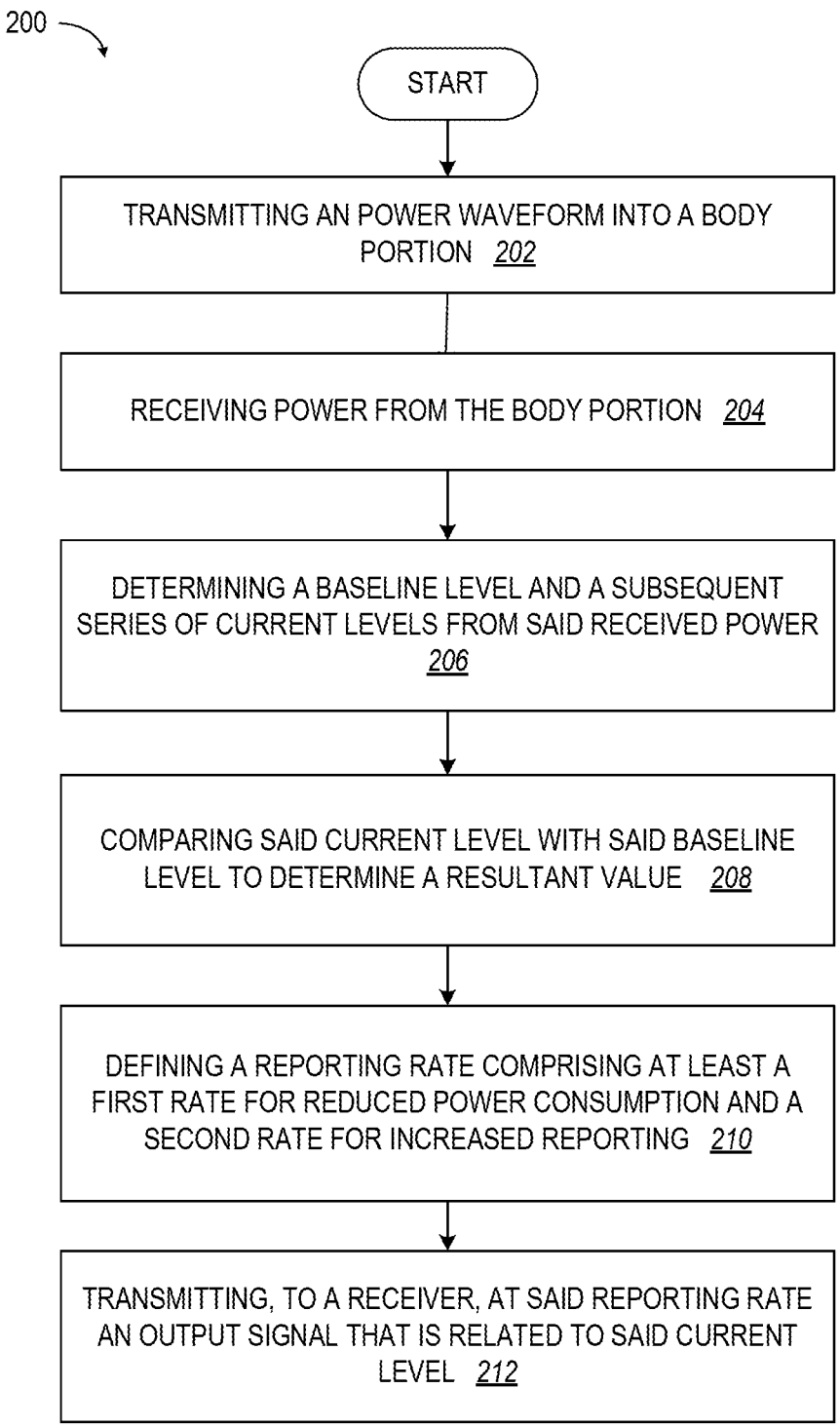
FIG. 2 is a flow diagram of a methodology for detecting a change in the fluid level of tissue with adjusted reporting rate, according to one aspect.

In FIG. 2, a method 200 provides for detecting a change in a level of fluid in tissue of a body. An power waveform is transmitted into a body portion (block 202). Power is received from the body portion (block 204). A baseline received power level and a subsequent series of current received power levels are determined from the received power (block 206). The current level is compared with the baseline level to determine a resultant value (block 208). A reporting rate is defined, comprising at least a first rate for reduced power consumption and a second rate for increased reporting (block 210). An output signal is transmitted at the reporting rate that is related to the current level to a receiver (block 212).

In an illustrative implementation, reducing power consumption by using a very low duty cycle for operation allows for a more economical device with a longer service life. With IV (intravenous) infiltrations, the fluid flow rate is typically low and therefore the infiltration of fluid leakage into the subcutaneous tissue outside of a vein is very slow as well. Therefore, by allowing a setting of intervals between performing one or more of quick sensor full-sweep operation, and wirelessly reporting can achieve performance benefits without degrading functionality. For example, it can be determined that a default or high rate of multiple times per second could be slowed to several times per minute. Multiple magnitudes of adjustability in a duty cycle could result in extremely low power consumption, extending the battery life of the device.

A nurse or technician may adjust, such as via the adjustment feature 144, a rate of activation of the detecting component 106 in relation to a rate of fluid injection so as to minimize power consumption. For example, presuming X volume of accidentally injected fluid within a patient is considered unacceptable, e.g., 2 ml, and fluid is being or about to be injected into the patient at a desired rate of Y volume/time, e.g., 1 ml/hour, then a nurse or technician may use the following formula to define a time period between activation events of the detecting component 106:

Time period between activation events of the detecting component 106=[X volume of unacceptable injected fluid]/[injection rate of Y volume/time] ÷2 (Safety factor).

The rate of activation of the detecting component (number of activations per unit time)=1/time period between activation events of the detecting component.

It is also contemplated that the signal processing component 118 may be used to determine the rate of activation of the detecting component 106 using the above formulas after a nurse or technician has input an unacceptable injected volume (X volume) and the current fluid injection rate (Y volume/time).

Figure 3:
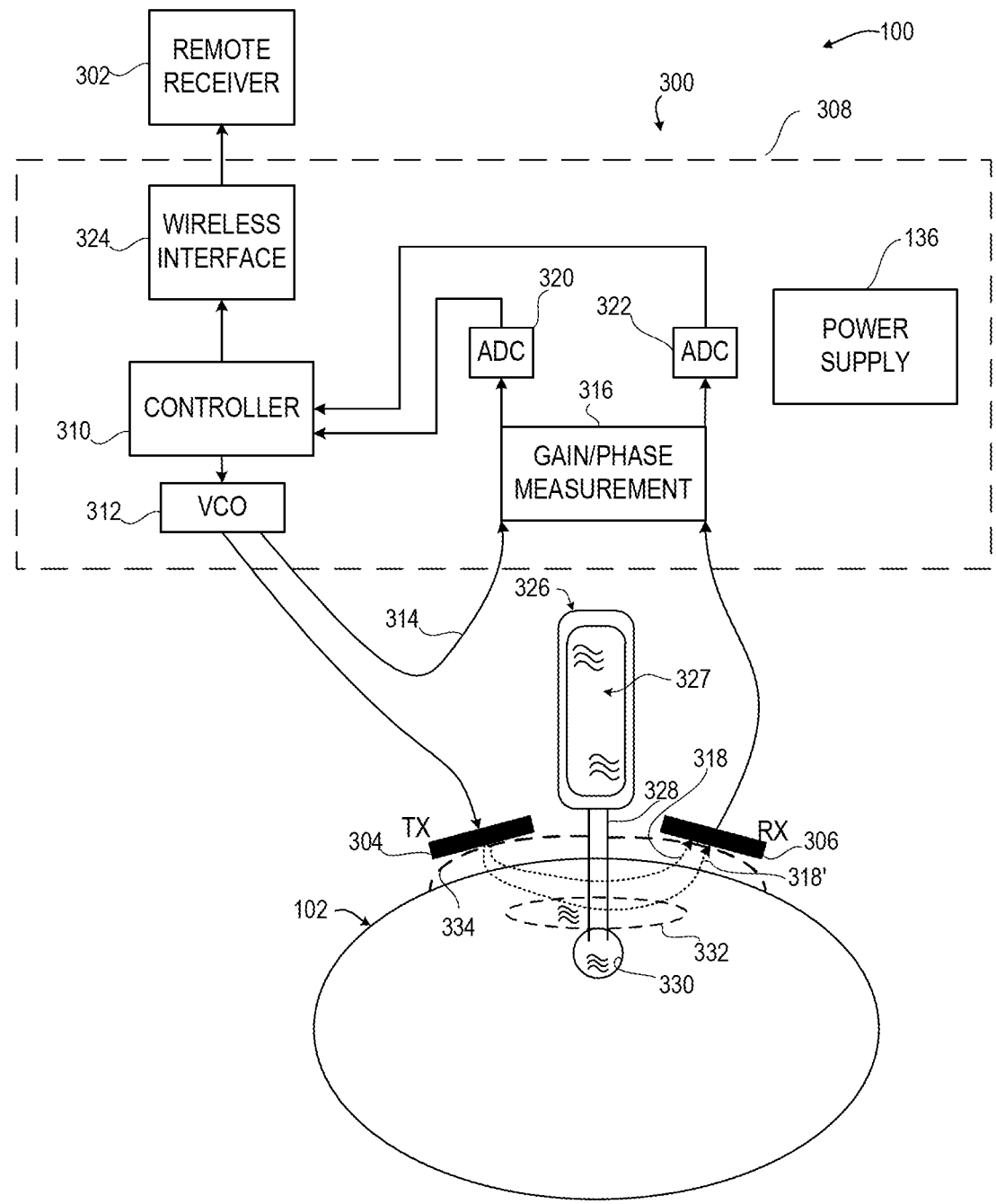
FIG. 3 is schematic block diagram of a system for detecting a change in a fluid level in tissue using a swept Radio Frequency (RF) power transmission, according to one aspect.

In FIG. 3, in an exemplary embodiment of the system 100, the device 104 and remote apparatus or receiver 124 (see FIG. 1) are depicted respectively as an RF device 300 and a remote receiver 302. The RF device 300 has RF transmit (TX) antenna(s) 304 that are driven and RF receive (RX) antenna(s) 306 that are read by an Application Specific Integrated Circuit (ASIC) or miniaturized, low-power circuitry 308 that performs at least portions of the functions of the detector component 106, signal processing component 118, and wireless interface 122 (FIG. 1).

To that end, a controller 310, such as a low-power microprocessor, Digital Signal Processor (DSP), or Field Programmable Gate Array (FPGA), sweeps across the RF frequency range of interest, such as 300 MHz to approximately 30 GHz, and more particularly up to 10 GHz, by driving an RF Voltage Controlled Oscillator (VCO) 312 or digital frequency synthesis circuit. The transmit antenna(s) 304 of the RF device 300 are then driven by the VCO 312 and the same signal is split as a reference signal 314 to a gain/phase measurement circuit/IC 316 (e.g., AD8302). The RX antenna(s) 306 return a signal corresponding to power 318, 318' (power 318' passes through fluid 332 in the patient) propagated through the tissue to the gain/phase measurement circuit/IC 316 which then sends voltages (representing gain/loss and phase information for the TX and RX signals) to two Analog-to-Digital Converters (ADC) 320, 322 which then digitize the corresponding gain and phase voltage information to the controller 310. The controller 310 can perform digital signal processing and direct a separate or integral wireless interface 324 to report to the remote receiver 302.

In use, a fluid supply 326 (e.g., infuser supply, contrast agent injector, IV drip, etc.) provides fluid 327 via a conduit 328 (e.g., catheter, needle, etc.) to a vascular body 330 of the body portion 102. As depicted at 332, extravasation or infiltration can cause an increase in a level of fluid that directly affects a signal 318' propagating through the tissue, such as based in a change in permittivity. Alternatively, a resulting change in dimensions of the body portion 102, as depicted at 334, can cause a change in the signal 318'.

The reference signal 314 is provided to compensate for the signal generated by the VCO 312, which may vary over time or may change in the transmission pathway extending up to the RX antenna(s) 306.

In order to sense an extravasation or infiltration, the controller 310 compares a first ratio of the returned signal from the RX antenna(s) 306 to the reference signal 314 (during fluid injection into a patient) with a second ratio of the returned signal from the RX antenna(s) 306 to the reference signal 314 (taken during a baseline detection operation, e.g., just before fluid is injected into the body portion). The first ratio defines a current received power level during patient fluid injection, while the second ratio defines a baseline received power level. When the first ratio is equal to or less than a predefined percentage, e.g., 90% or less, of the second ratio, then the controller 310 determines that an unacceptable fluid level change, i.e., an unacceptable extravasation/infiltration, has occurred.

Figure 4:
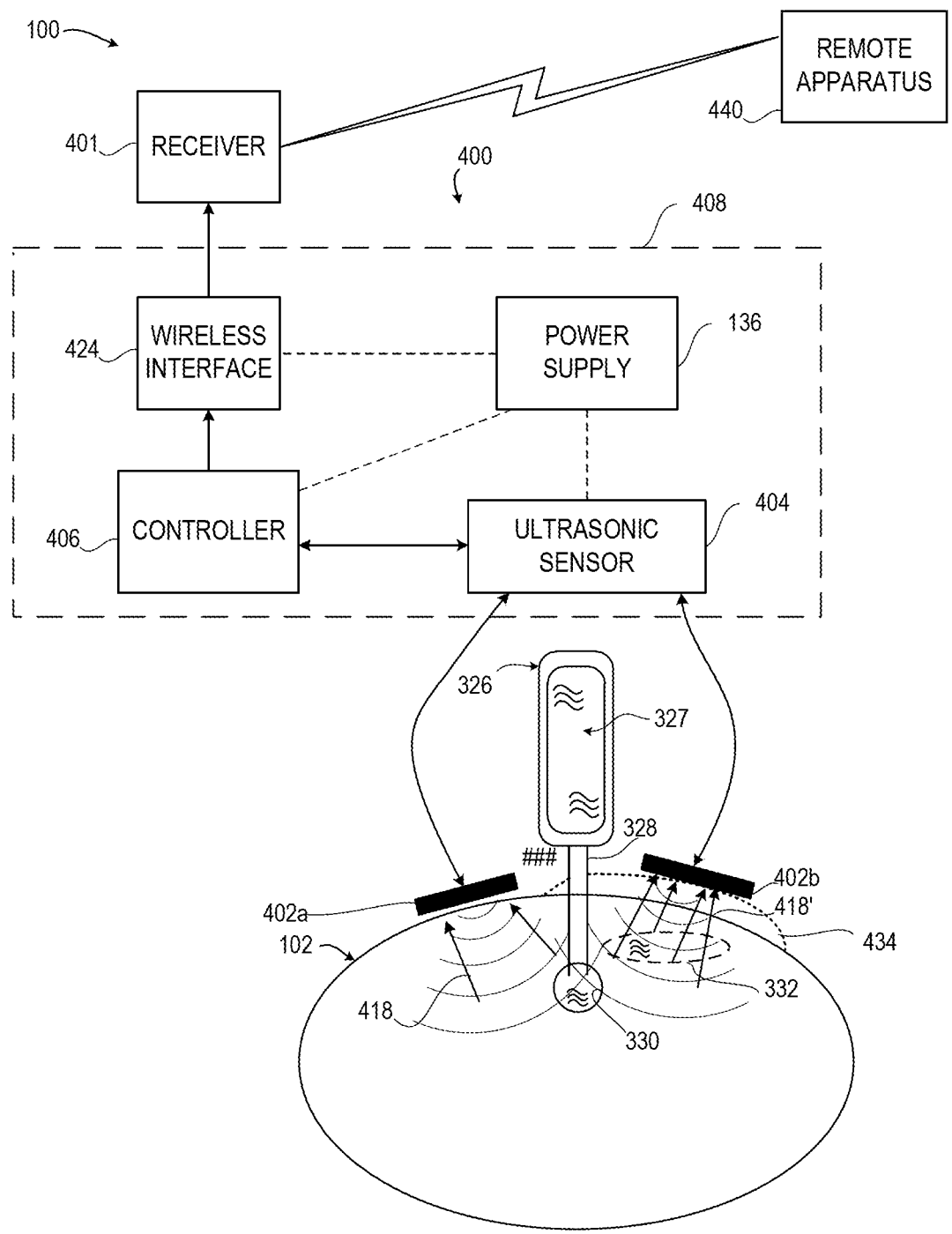
FIG. 4 is a schematic block diagram of a system for detecting a change in a fluid level in tissue using an ultrasonic power transmission, according to one aspect.

The rate at which the RF device 300 is active (e.g., rate of RF sweeps, rate of reports, etc.) can be optimized between power consumption and a prudent rate of monitoring in order to extend the service life of the power supply In FIG. 4, in another exemplary embodiment of the system 100, the device 104 and remote apparatus or receiver 124 are depicted respectively as an ultrasonic device 400 and a remote receiver 401. In one aspect, an ASIC or miniaturized, low-power circuitry 408 performs at least portions of the functions of the detector component 106, signal processing component 118, and wireless interface 122 (FIG. 1). The ultrasonic device 400 has ultrasonic transceiving antenna(s) 402a, 402b that are driven and are read by an ultrasonic sensor 404 under the control of a controller 406 that reports via a wireless interface 424.

In use, the fluid supply 326 (e.g., infuser supply, contrast agent injector, IV drip, etc.) provides fluid 327 via the conduit 328 (e.g., catheter, needle, etc.) to a vascular body 330 of the body portion 102. In a baseline state, the ultrasonic transceiving antenna(s) 402a transmits and receives an ultrasonic signal 418. Extravasation or infiltration can cause an increase in a level of fluid, as depicted at 332, that directly affects an ultrasonic signal 418' sensed by the ultrasonic transceiving antenna(s) 402b due to a resulting change in dimensions of the body portion 102, as depicted at 434, or due to acoustic properties of the fluid relative to surrounding tissue.

In another exemplary aspect, the ultrasonic device 400 is worn by a patient that is ambulatory or otherwise mobile. The wireless interface 424 comprises a Personal Access Network (PAN) interface, such as BLUETOOTH, that communicates with a remote apparatus 440 via a receiver 401 having a cell phone link, such as a Publicly Switched Telephone Network (PSTN) number for Machine-to-Machine (M2M) reporting to a hospital outpatient monitoring system.

While the foregoing disclosure discusses illustrative aspects and/or embodiments, it should be noted that various changes and modifications could be made herein without departing from the scope of the described aspects and/or embodiments as defined by the appended claims. Furthermore, although elements of the described aspects and/or embodiments may be described or claimed in the singular, the plural is contemplated unless limitation to the singular is explicitly stated. Additionally, all or a portion of any aspect and/or embodiment may be utilized with all or a portion of any other aspect and/or embodiment, unless stated otherwise.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein, will only be incorporated to the extent that no conflict arises between that incorporated material and the existing disclosure material.

What is claimed is:

1. An apparatus for indicating a fluid level change in a body portion, said apparatus comprising:
   a detecting component comprising a transmit antenna configured to transmit power into said body portion and a receive antenna configured to receive power passing through said body portion as received power, wherein said power transmitted by said transmit antenna is split into a first portion that is transmitted into said body portion and a second portion that comprises a reference signal;
   a signal processor configured to compare said received power with a baseline received power and to generate an output signal based at least in part on said received power, wherein:
      said baseline received power is defined by a first ratio of a returned power signal relative to said reference signal during a baseline detection,
      said received power is defined by a second ratio of a returned power signal relative to said reference signal during fluid injection into said body portion, and
      a change in said received power, when compared with said baseline received power, is indicative of said fluid level change;
   a wireless interface configured to transmit, to a receiver, said output signal from said signal processor; and
   a power supply configured to power said detecting component and said wireless interface,
   said detecting component further comprising:
      a controller configured to intermittently cause power to be transmitted into said body portion; and
      the controller further configured to set a rate of activation of said detecting component, wherein activation of the detecting component causes power to be transmitted into the body portion, the rate of activation being optimized between power consumption and a prudent rate of monitoring for a change in a level of fluid in tissue, wherein said prudent rate of monitoring relates to a fluid injection rate and an unacceptable volume of accidentally injected fluid.

2. The apparatus of claim 1, wherein said wireless interface intermittently transmits said output signal.

3. The apparatus of claim 1, further comprising a substrate supporting said detecting component and said wireless interface.

4. The apparatus of claim 3, wherein said power supply comprises a portable power supply supported by said substrate.

5. The apparatus of claim 1, wherein said transmit antenna is configured to transmit power comprising a Radio Frequency (RF) signal and said receive antenna is configured to receive power comprising an RF signal.

6. The apparatus of claim 5, wherein said transmit antenna comprises an RF voltage controlled oscillator for sweeping a frequency range of greater than 1.5 GHz to approximately 10 GHz over a period of time.

7. The apparatus of claim 5, wherein said receive antenna comprises a gain/phase measurement circuit.

8. The apparatus of claim 1, wherein said transmit antenna is configured to transmit power comprising an ultrasonic signal and said receive antenna is configured to receive power comprising an ultrasonic signal.

9. The apparatus of claim 1, wherein said wireless interface comprises at least one of a personal area network interface, a Wi-Fi interface, or a cellular interface.

10. The apparatus of claim 9, wherein said wireless interface comprises said personal area network interface for interfacing to a cellular device for communicating with said receiver.

11. The apparatus of claim 1, further comprising a conduit for providing fluid to said body portion.

12. The apparatus of claim 11, further comprising a substrate supporting said detecting component, said signal processor, said wireless interface, and said conduit.

13. The apparatus of claim 11, further comprising a substrate supporting said detecting component, said signal processor, and said wireless interface, wherein said conduit is positioned near said substrate.

14. The apparatus of claim 1, wherein said controller comprises a manual adjustment feature.

15. A system for indicating a fluid level change in a body portion, said system comprising:
    a device comprising:
        a detecting component comprising a transmit antenna configured to transmit power into said body portion and a receive antenna configured to receive power passing through said body portion as received power, wherein said power transmitted by said transmit antenna is split into a first portion that is transmitted into said body portion and a second portion that comprises a reference signal;
        a signal processor configured to generate an output signal based at least in part on said received power;
        a wireless interface configured to transmit said output signal from said signal processor; and
        a power supply configured to power said detecting component, said signal processor, and said wireless interface,
    said detecting component further comprising:
        a controller configured to intermittently cause power to be transmitted into said body portion; and
        the controller further configured to set a rate of activation of said detecting component, wherein activation of the detecting component causes power to be transmitted into the body portion, the rate of activation being optimized between power consumption and a prudent rate of monitoring for a change in a level of fluid in tissue, wherein said prudent rate of monitoring relates to a fluid injection rate and an unacceptable volume of accidentally injected fluid; and
    a remote apparatus comprising a receiver configured to receive said output signal from said wireless interface,
    wherein a baseline received power is defined by a first ratio of a returned power signal relative to said reference signal during a baseline detection,
    wherein said received power is defined by a second ratio of a returned power signal relative to said reference signal during fluid injection into said body portion, and
    wherein a change in said received power, when compared with said baseline received power, is indicative of said fluid level change.

16. The system as set forth in claim 15, wherein said remote apparatus further comprises a controller configured to:
    compare said received power with said baseline received power to produce a comparison result; and
    generate a fluid level change indication based upon said comparison result.

17. The system as set forth in claim 15, wherein said controller is further configured to:
    compare said received power with said baseline received power to produce a comparison result; and
    generate said output signal based upon said comparison result.

18. The system of claim 15, further comprising a conduit for providing fluid to said body portion.

* * * * *